US007734480B2

(12) United States Patent
Stangel

(10) Patent No.: US 7,734,480 B2
(45) Date of Patent: Jun. 8, 2010

(54) CLINICAL CARE UTILIZATION MANAGEMENT SYSTEM

(76) Inventor: Peter Stangel, 15 Forest Ridge Rd., Nyack, NY (US) 10960

( * ) Notice: Subject to any disclaimer, the term of this patent is extended or adjusted under 35 U.S.C. 154(b) by 1202 days.

(21) Appl. No.: 09/772,394

(22) Filed: Jan. 30, 2001

(65) Prior Publication Data

US 2002/0165735 A1 Nov. 7, 2002

Related U.S. Application Data

(60) Provisional application No. 60/247,246, filed on Nov. 13, 2000.

(51) Int. Cl.
*A61B 5/00* (2006.01)
(52) U.S. Cl. .............. 705/3; 705/2; 705/4; 705/67; 715/741; 707/3; 707/104.1; 706/45; 700/83; 600/300; 434/262
(58) Field of Classification Search ............ 705/2, 705/3, 4, 67; 715/506, 741, 516; 600/300; 713/600; 706/45; 434/262; 707/104.1, 3; 700/83; 348/207.1; 422/68.1
See application file for complete search history.

(56) References Cited

U.S. PATENT DOCUMENTS

| 4,667,292 | A | | 5/1987 | Mohlenbrock et al. |
|---|---|---|---|---|
| 4,878,175 | A | * | 10/1989 | Norden-Paul et al. .......... 705/2 |
| 5,253,164 | A | | 10/1993 | Holloway et al. |
| 5,301,105 | A | * | 4/1994 | Cummings, Jr. .............. 705/2 |
| 5,410,704 | A | * | 4/1995 | Norden-Paul et al. ....... 718/101 |
| 5,471,382 | A | * | 11/1995 | Tallman et al. ............. 600/300 |
| 5,557,514 | A | | 9/1996 | Seare et al. |
| 5,574,828 | A | * | 11/1996 | Hayward et al. ............ 706/45 |
| 5,664,109 | A | * | 9/1997 | Johnson et al. .............. 705/2 |
| 5,764,923 | A | * | 6/1998 | Tallman et al. ............... 705/3 |
| 5,772,585 | A | * | 6/1998 | Lavin et al. ................ 600/300 |
| 5,774,357 | A | * | 6/1998 | Hoffberg et al. ............ 713/600 |
| 5,933,136 | A | * | 8/1999 | Brown ...................... 715/741 |
| 5,933,809 | A | | 8/1999 | Hunt et al. |
| 5,946,659 | A | * | 8/1999 | Lancelot et al. .............. 705/3 |
| 5,950,190 | A | * | 9/1999 | Yeager et al. ................. 707/3 |
| 5,964,700 | A | * | 10/1999 | Tallman et al. ............. 600/300 |
| 5,974,389 | A | * | 10/1999 | Clark et al. ................. 705/3 |
| 5,991,728 | A | | 11/1999 | DeBusk et al. |
| 6,018,713 | A | * | 1/2000 | Coli et al. ................... 705/2 |
| 6,047,259 | A | * | 4/2000 | Campbell et al. ............. 705/3 |
| 6,049,794 | A | * | 4/2000 | Jacobs et al. ............... 706/45 |
| 6,117,073 | A | * | 9/2000 | Jones et al. ................ 600/300 |
| 6,177,940 | B1 | * | 1/2001 | Bond et al. ................ 434/262 |

(Continued)

OTHER PUBLICATIONS

"A Web-Enabled Framework For Smart Card Application in Health Care" Chan et al, Sep. 2001, Communications Of The ACM, 44, 9, 76, Dialog File 149, Acc. No. 02021813.*

*Primary Examiner*—Luke Gilligan
*Assistant Examiner*—Dilek B Cobanoglu
(74) *Attorney, Agent, or Firm*—Greenberg Traurig LLP

(57) ABSTRACT

A computer implemented system facilities the submission of clinical events data to a reviewing agency by prompting for data needed to authorize the appropriateness of the event. The system directs an appropriate submission to authorize the event. The system further stores the patient clinical event data and presents the data for review. The system confirms that the clinical event is appropriate by referring to the input data and predetermined validation rules.

9 Claims, 13 Drawing Sheets

U.S. PATENT DOCUMENTS

| | | | |
|---|---|---|---|
| 6,230,142 B1 * | 5/2001 | Benigno et al. | 705/3 |
| 6,234,964 B1 * | 5/2001 | Iliff | 600/300 |
| 6,308,171 B1 * | 10/2001 | De La Huerga | 707/3 |
| 6,341,265 B1 * | 1/2002 | Provost et al. | 705/4 |
| 6,381,611 B1 * | 4/2002 | Roberge et al. | 707/104.1 |
| 6,484,144 B2 * | 11/2002 | Martin et al. | 705/2 |
| 6,597,392 B1 * | 7/2003 | Jenkins et al. | 348/207.1 |
| 6,602,469 B1 * | 8/2003 | Maus et al. | 422/68.1 |
| 7,092,914 B1 * | 8/2006 | Shear et al. | 705/67 |
| 2001/0012913 A1 * | 8/2001 | Iliff | 600/300 |
| 2001/0037218 A1 * | 11/2001 | Kaker et al. | 705/2 |
| 2001/0042080 A1 * | 11/2001 | Ross | 707/506 |
| 2001/0051881 A1 * | 12/2001 | Filler | 705/3 |
| 2002/0151992 A1 * | 10/2002 | Hoffberg et al. | 700/83 |

* cited by examiner

Inpatients

| Facility Types... ▾ | Acute Care |
|---|---|

Facilities... ▾ — 28

General Hospital — 27    [ NEW ADMIT ] — 31    3 Patients

◉ Admit Clinical Screen ← 32

○ CLINICAL SCREEN    ○ Discharge Plan Screen

| LAD | Reduced | Last Note | Admit | Adm Auth No | Discharge Plan | Patient |
|---|---|---|---|---|---|---|
| Pending | None | None | 11/05/00 | Pending | None | West Ronald |
| Pending | None | None | 11/05/00 | Pending | None | Brown Paul |
| Pending | None | None | 11/04/00 | Pending | None | Smith Jane |

[ HOME ]

FIG 2A

ADMISSION FACE SCREEN

| Member | ID: ff55555f | Last Name: Gray | First Name: Jane |
|---|---|---|---|
| | Birthdate 11/4/50 | ○ Male ; ● Female | |
| | Group No A77 | Product Commercial | Contract No GG234 |

☐ Related to accident or 3rd party liability

| Admit Date | 11/5/200 | Today ◆ | | |
| --- | --- | --- | --- | --- |
| Came from | Home ◆ | | Arrived via | Auto ◆ |
| Attending MD | Phil Byrd MD | ◆ | | |
| Admitting MD | Susan Winters | ◆ | | |
| | ICD9 Groups ◆ | | | |
| | ICD9 Codes ◆ | Code: ☐ | | |
| Admit Dx | ◆ | | | |

[SUBMIT (->Census)] [SUBMIT (->Clinical)] [RESET]

Chart Notes
ICD-9 Codes  Admission: 486 Pneumonia  ◄ ►
CPT-4 Codes  ◄ ►
History  Dx: 486 Pneumonia: Last Hospital Admit 8 months ago
         Dx: 491.3 Asthma: Last Hospital Admit 2 years ago; Last ER Visit 4 days ago  ◄ ► 81
Present Illness  ◄ ►
Exam  ◄ ►

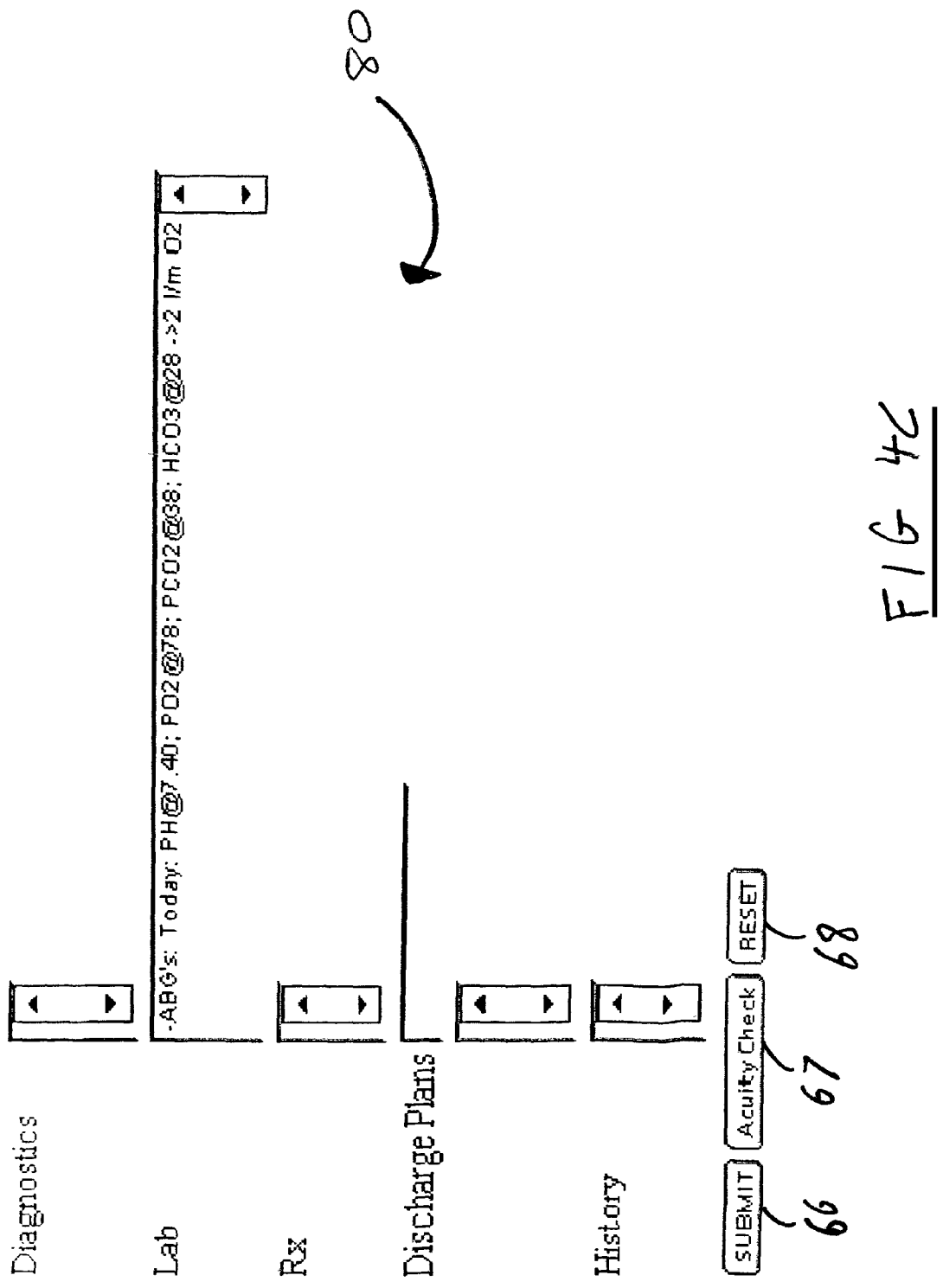

Patient Smith Jane     ID: AA1111A   Admit Date 11/4/00
Female- DOB 10/15/70                 Admit Dx [↔]

71 →

Disposition [Home_____]

[Home ↔] 73
[DME ↔] 74
[E1200 wheelchair ↔] 75

[↔] 72

-DME: E1200 wheelchair
-DME: E1000 Oxygen (tank)   ← 76
                             ← 77
[☑ E1200 wheelchair]   [New]
  78

79 →

Home Visits: [__] visit(s) over: [__] weeks / OR / [__] days / (Visit Duration [__] hrs)

Vendors
[VendorLocations ↔]  85
[↔] 84    [GET]

☐ Name _____
Address _____
City _____  State [__]  Zip [__]
Contact   Last Name _____  First Name _____
          Telephone [___]-[____]  Ext.[__]  //Fax [___]-[____]
          E-Mail Address _____

86 →

PIN No [_____]

[SUBMIT]  [Check for Auth]  [RESET]  [Discharge Order... ↔]  [DISCHARGE]
  87           88             89              90                 91

FIG 5A

Chart Notes

Discharge Plans | ·DME: E1200 wheelchair
                | ·DME: E1000 Oxygen (tank)

Clinical Status | ·Incomplete IV Rx
                | ·Ambulates <15 feet

Clinical Needs

Exam

Patient: West Ronald  ID: cc33333c  Admit Date 11/5/00  ← 71
- DOB 00/00/00    Admit Dx [◆] ← 72

Disposition [Skilled Nursing ◆]

Skilled Nursing [◆] ← 73
Accepting Facility Status [◆] ← 74
Needs PRI submission [◆] ← 75

-Skilled Nursing: Needs PRI submission@Sunrise Nursing Home   [◀▶] ← 76

☑ Needs PRI submission  [New] ← 77
  ↑ 78

Home Visits: [  ] visit(s) over: [  ] weeks / OR / [  ] days / (Visit Duration [  ] hrs)

Vendors
[Nyack ◆]
[Sunrise Nursing Home ◆]  [GET]
        ↑ 84        ↑ 85

☑ Name [Sunrise Nursing Home]                    ← 86
  Address [                    ]
  City [           ] State [   ] Zip [   ]
  Contact Last Name [        ] First Name [       ]
  Telephone [        ] - [      ] Ext. [   ] / /Fax [   ]
  E-Mail Address [                    ]

[SUBMIT] [Check for Auth] [RESET] [Discharge Order... ◆] [DISCHARGE]
   ↑87       ↑88           ↑89         ↑90              ↑91

FIG 5C

CLINICAL CARE UTILIZATION MANAGEMENT SYSTEM

PRIORITY CLAIM

This application claims priority to U.S. Provisional Patent Application No. 60/247,246, filed on Nov. 13, 2000, entitled "UMsource Software," designating Peter Stangel as the inventor.

FIELD OF THE INVENTION

The present invention related to data processing systems. Particularly, the invention relates to a clinical care utilization management system.

BACKGROUND

Clinical care rendered by physicians and other health care providers is reviewed for utilization management, quality of care, and other review or analytic functions by reviewing entities charges with these functions. Utilization management is usually performed by a health maintenance organization (HMO) or other managed care organization (MCO).

When a healthcare provider (HCP) examines and treats a patient, the HCP records the examination in a clinical chart. Under industry custom, designated personnel at the health care site extract clinical information from the chart and transmit the clinical data to the reviewing entity by telephone or fax.

At the reviewing organization, personnel manually input this clinical data into an electronic form with one or more text fields. The information is then reviewed by one or more professional personnel to determine appropriateness of care. Determinations of the appropriateness of care are then communicated back to the health care site by phone or fax (negative determinations also require a formal letter of denial).

Moreover, because the clinical information has been electronically input into text fields without any format, the reviewing organization lacks the ability to electronically evaluate this data for appropriateness of care. Determinations are made manually. Determinations are often inconsistent for similar clinical situations by the same reviewer or among multiple reviewers. There is almost no way to systematically evaluate this data among multiple clinical episodes to see patterns of care.

As may be gathered from the description above, the process for submitting and reviewing clinical records is cumbersome and time consuming. Both the HCP and the MCO dedicate personnel and other resources to the sole task of managing and processing clinical data. Accordingly, there is a need for a system that facilitates the generation and processing of clinical records, which provides sufficient data to the MCO, and which facilitate the speedy processing and authorizing of the records.

SUMMARY OF THE INVENTION

The invention provides for a centralized system for the submission and automatic processing of clinical care transactions over the Internet. The MCO contracts with a utilization management organization that employs the invention to facilitate the utilization management functions. The MCO agrees on the utilization criteria that are automatically applied by the utilization system. Health care sites are granted access to the utilization system. The health care site employs the utilization system to submit clinical transaction data. The utilization system automatically process the data and determines whether the transaction is authorized by following the agreed upon utilization criteria. The date is then further submitted to the MCO for record keeping and further review if the transaction has not been automatically authorized.

In one embodiment, the invention provides a computer implemented system for generating a medical diagnosis clinical record for submission to a MCO. The system includes a data entry interface, which facilitates the entry of data corresponding to a clinical event corresponding to the clinical diagnosis for that event. The system also includes at least one selection interface, which is adapted to facilitate the selection of at least one diagnosis. Further, the system includes a navigation module, which facilitates the identification of fields for which data should be entered. The navigation module facilitating the identification of the fields in response to the selection from the selection interface. A verification module determines the authorization level for the diagnosis by referring to at least the data in the directed-to fields. The verification module determines the authorization level prior to the submission of the record to a processing module. The invention further facilitates the submission of clinical data over Intranets and other proprietary networks.

In another aspect of the invention, there is provided a utilization management system that authorizes a diagnosis by directing the user to enter all of the required data so as to generate a sufficient clinical encounter record to evaluate the record for appropriateness of care. The system also automatically evaluates the entered data to determine an authorization level. The system includes a user interface to facilitate the submission of data to the system. The user interface is associated with a forms database that is used in generating the user screens by which data is entered. The user interface is also coupled to a navigation module that guides the user interaction with the user screens. The navigation module is associated with a selection database that provided information as to the data selections that should be available to a user. The user interface is also coupled to a verification module that is used to determine a level of authorization and criteria compliance based on the entered data. The verification module is associated with a criteria database that stores criteria rules, which are evaluated to determine an authorization level.

In another embodiment, the system facilitates the generation of encounter records that are adapted for automatic authorization processing by a remote system. The encounter records include all the data required for determining an authorization level. The encounter records further provide the data is an objective format that can be evaluated without the aid of a human operator.

In yet another embodiment, the invention provides a two step method for entering medical diagnosis data. The method includes entering a criteria into the system. The criteria corresponds to a rule required for authorizing a diagnosis. The criteria is also associated with at least one finding. Finally, the method includes entering a finding into the system.

The present invention also provides an interface for entering data for the authorization of a diagnosis. The interface includes a first portion, which is adapted to facilitate the selection of a system group. The interface includes a second portion, which is adapted to facilitate the display and entry of data for the diagnosis. A display area is included within the second portion, which is displaying parameter and corresponding findings for the selected system group from the first portion. Finally, the interface includes a data entry area, which is facilitating at least the selection of findings and parameters for the system group.

The invention also provides a system where date is entered directly during the clinical event on hand-held devices that are coupled to a remote database by a network interface so as to create a clinical record of the encounter and replace paper clinical charting. In one embodiment, the hand-held devices are coupled to the utilization system by a mobile network connection.

The present invention also provides an interface for the authorization of clinical care including hospital admission, acuity of level of care for inpatient hospital days, appropriateness of emergency room visits, and preauthorization of elective medical services and hospitalizations.

In another embodiment, a system in accordance with the invention is implemented as a web based system for submitting requests for automatic authorization. A health care facility employs a web navigation interface, such as a browser, to connect to the web based system. Pages are provided to facilitate the entry of encounter date. The data is processed to provide an authorization indication before the pages are submitted.

APPENDIX

The specification includes an appendix, Appendix A, which illustrates a hierarchal arrangement for an Elements Tree structure of the invention. The appendix is intended to serve as an integral part of the disclosure, which is provided in this specification.

BRIEF DESCRIPTION OF THE DRAWINGS

FIG. 2A illustrates an Inpatient Census screen;

FIG. 2B illustrates an Admission Face screen;

FIG. 3A illustrates an Admission Clinical screen;

FIG. 3B illustrates a chart section of the Admission Clinical screen of FIG. 3A;

FIG. 4C is a continuation illustration of the chart section of FIG. 4B;

FIG. 5A illustrates a Patient Discharge screen;

FIG. 5B illustrates a chart section of the Patient Discharge screen of FIG. 5A;

FIG. 5C illustrates the Patient Discharge screen when post discharge treatment is selected for the patient.

DETAILED DESCRIPTION

The structure and operation of a utilization system in accordance with the invention will now be discussed with reference to illustrations of an exemplary utilization system. First, the structure and operation of system modules will be discussed with reference to an illustration of a system arrangement. Next, the structure and operation of the system's data entry interfaces will be discussed with reference to illustrations of user screens from a web based utilization system. Finally, the operation of the system when submitting encounter data is illustrated with reference to user screens and a flow diagram of user interaction steps.

The present discussion refers to data entry operations in the context of in the context of user interaction with the system. Such data entry operations are not limited to the entry of a textual or numerical values in an entry box but also include the selection of data from a pop-up list, the selection of a radio button from a set of buttons, the acquiescence of a user with default data that is automatically filled by the system, and a check indication in a check box. As may be appreciated, other forms of providing data are available and are intended to be encompassed within the present discussion when referring to data entry.

The present discussion refers to a "user" interacting with the system. The term "user" is intended to encompass an individual member of an organization that interacts with the system, several members of the organization interacting with overlapping portions of the system, or members of different organizations interacting with various portions of the system. Moreover, as may be appreciated, a "user" includes a computer or otherwise automated system that submits data to a processing system of the invention.

Figure 1:
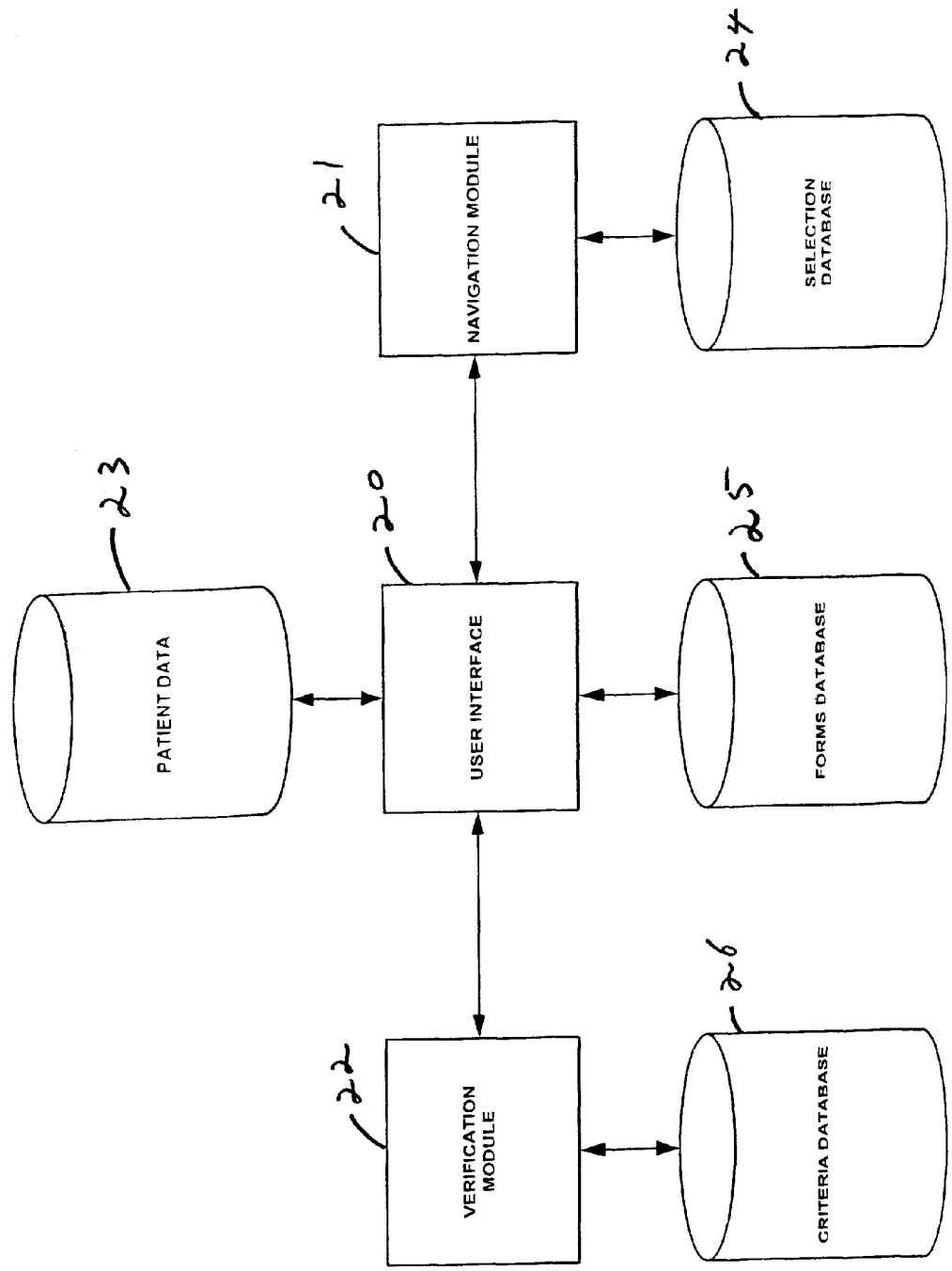
FIG. 1 illustrates the logical arrangement of modules in a utilization management system in accordance with the invention.

FIG. 1 illustrates the logical arrangement of modules in a utilization system in accordance with the invention. The modules include a user interface 20, a navigation module 21, and a verification module 22. The user interface 20 generates the user screens with which the user interacts to submit or review data. The user interface is preferably coupled to a communication link (not shown) that receives user commands and data from a network connection. In one embodiment, the communication link is an Internet connection. In another embodiment, the communication link is a local area network connection. In yet another embodiment, the communication link is a mobile, wireless, remote Internet link. In yet another embodiment, the communication link is a proprietary link.

The user interface 20 preferably facilitates the generation of user screen in accordance with predetermined screen templates and controls. The predetermined templates and controls are advantageously stored in a forms database 25. The user interface 20 is further associated with a patient data storage module 23, which stores patient data that was entered and submitted to the system. The patient data storage module 23 also stores general data relating to health care providers, health care facilities, and MCOs. The user interface 20 is operatively coupled to the verification module 22 and to the navigation module 21.

The navigation module 21 is employed to guide the user in entering data by modifying fields of the user screen in response to the user entering data that affects the navigation path available to the user. Preferably, the navigation module 21 communicates with the user interface 20 to identify when the user enters data that affects the navigation path or otherwise entails a modification of available controls. The navigation module 21 is associated with a selection database 24. The selection database 24 preferably includes data that identifies members of each hierarchal level and the logical relation between levels. Such arrangement of members and relations is illustrated in Appendix A. The example arrangement of Appendix A is for a four tier division. However, as may be appreciated, different number of tiers are used in other implementations of the invention.

The verification module 22 examines the input data to determine whether an authorization status or a criteria status should change in response to the input data. The verification module 22 is preferably associated with a criteria database 26. The criteria database 26 stores rules corresponding to criteria, which are applied to determine whether a clinical event should be authorized. The criteria are preferably in the form of Boolean rules that refer to data fields of the user screens. In one embodiment, the data for each field of the user screen is provided to the verification module 22 after the user modifies the data in the particular field. In another embodiment, selected fields of the user screen are designated to trigger the submission of data to the verification module 22.

In operation, the system provides user screens to the user by employing the user interface 20. The user screens include textual displays and data entry controls that facilitate the submission of data. Some of the screens presented to the user are static screens, whereby the same screen is provided to the user regardless of the data entered by the user. Other screens are dynamic screens, whereby the selections and data entry interfaces depend on previously entered data. In one embodiment, the dynamic screens are generated when the user interface 20 employs data from the navigation module 21 in combination with controls and form templates from the forms database 25.

The navigation module 21 preferably receives selections from the user interface 20. The navigation module 21 responds to predetermined user selections by querying the selection database 24. In one embodiment, a user selection of a criteria from a criteria pop-up list (discussed below) is received by the navigation module 21, which responds by searching for the associated element, group, parameter, and findings. In one embodiment, when the user selects a criteria, the navigation module 21 queries the database 24 for the corresponding criteria attributes for which data is required. The elements database 24 returns selections that are available to the user as a result of the newly entered data. The navigation module 21 communicates with the user interface 20 to modify the available selections in the user screen to conform to the changed navigation path. In one embodiment, an element, a group, a parameter, and a finding are automatically set in response to the selection of a criteria from a criteria pop-up list (discussed below).

The verification module 22 receives user data and determines whether the data is sufficient to authorize the clinical event or to satisfy a particular criteria of the clinical event. The rules in the criteria database 26 preferably include both rules that examine data from a single field and rules that examine data from several fields. Rules are advantageously structured to progressively determine, first, when a particular criteria is satisfied and, second, when a displayed diagnosis is authorized. Advantageously, rules are progressively applied to other diagnosis of the clinical event, when the particular displayed diagnosis is not authorized. Preferably, the rules employ Boolean functions and evaluations to define when a criterion or diagnosis is satisfied. In one embodiment, data items are combined by using Boolean operators such as AND, OR, and NOT. When the user data is sufficient to authorize a diagnosis or satisfy a criteria, the system provides a corresponding indication to the user. The indication is preferably provided prior to the user submitting the record to the utilization system. Accordingly, the verification operation is local to the user. In one embodiment, the verification is automatically prompted when the user navigates from one screen of the system to another and screen data has changed.

Preferably, the authorization criteria are set by the agency for which the record is intended. The rules are advantageously set by selecting from several sets of rules or by independently creating rule sets. As may be appreciated, different agencies may desire different rules. Thus, a user that is a customer of an agency is provided access to the system and is authorized in accordance with that agency's rules. The rules that are used for criteria and authorization evaluation are advantageously hidden from the user and are only available to authorized personal such as the MCO or the utilization system administrator.

The rule application portion of the utilization system preferably includes rules for criteria and rules for authorization levels. Criteria rules are used to evaluate whether the entered data satisfies a particular criteria that is applicable to the overall authorization evaluation. The diagnosis authorization rules advantageously refer to the results of criteria evaluations to determine the result and authorization level. The criteria rules evaluate the completeness of data in addition to evaluating whether the data satisfies a criteria. As may be appreciated, there can be more than one criteria for a given diagnosis authorization. However, at times, a diagnosis is only associated with a single criteria. The criteria preferably correspond to major symptoms as well as to the diagnosis.

In one embodiment, the criteria rule results are indicated by a message in a dialog box of the entry form. In another embodiment, the result indication is by an alert window that is provided when invalid data is entered.

In one implementation of the utilization system, the modules and databases are part of a database application written on a $4^{TH}$ DIMENSION, ACI database and with HTML and JAVA Script interfaces. In another implementation, the database application is a front-end for a mainframe database. Preferably, the database application is SSL enabled to provide for transmission security over the Internet. The database includes proprietary encryption for transmission over its proprietary network.

FIG. 2A illustrates an Inpatient Census screen 29 of a utilization system in accordance with the invention. A facility identification portion of the screen includes a facility type pop-up list 30 to select a facility type. The facility identification portion also includes a facility pop-up list 31 to identify a facility from facilities in the network of the selected facility type. The Inpatient Census screen 29 also includes navigation buttons 32 for navigating to an Admit Clinical Screen, a Clinical Screen, and a Discharge Plan Screen. A New Admit button 27 facilitates navigation to an initial administrative patient registration screen (Admission Face screen). Finally, the Inpatient Census screen 29 includes a display box 33 that displays patient record data for the selected facility for the current date. In one embodiment, the displayed patients are all patients belonging to the MCO that are hospitalized in the facility. In another embodiment, the displayed data is for all inpatients at the facility. The display box 33 preferably includes, for each patient, the last acute day authorized, the number of days not authorized, last date that clinical data was input, admission authorization number, and discharge plan with corresponding discharge plan authorization status.

In operation, the user selects a facility type from the facility type pop-up list 30. The user then selects a facility from the facility pop-up list 31. The facility name is displayed in the corresponding display box 28. Patient data for patients that are in the facility during the default period are displayed in the display box 33. The user selects a patient record from a line of the display box 33. The user then selects one of the navigation buttons 32 to prompt the corresponding user screen for the selected patient record.

FIG. 2B illustrates an Admission Face screen of a utilization system of the invention. The Admission Face screen is used to enter patient data for a newly admitted patient. Such data includes ID number, name, gender, date of birth, admission date, attending doctor name, ICD-9 code, admission diagnosis, and any other relevant patient information.

In general, when a patient is admitted to a facility, an administrative admission record is created in the Admission Face screen. An Admission Clinical screen is then employed to submit data for creating and to review an admission clinical record. A daily inpatient clinical record is created and reviewed by employing a Clinical screen. Finally, a discharge planning record is created and reviewed at any time after admission, but preferably early in the hospitalization.

Figure 3A:
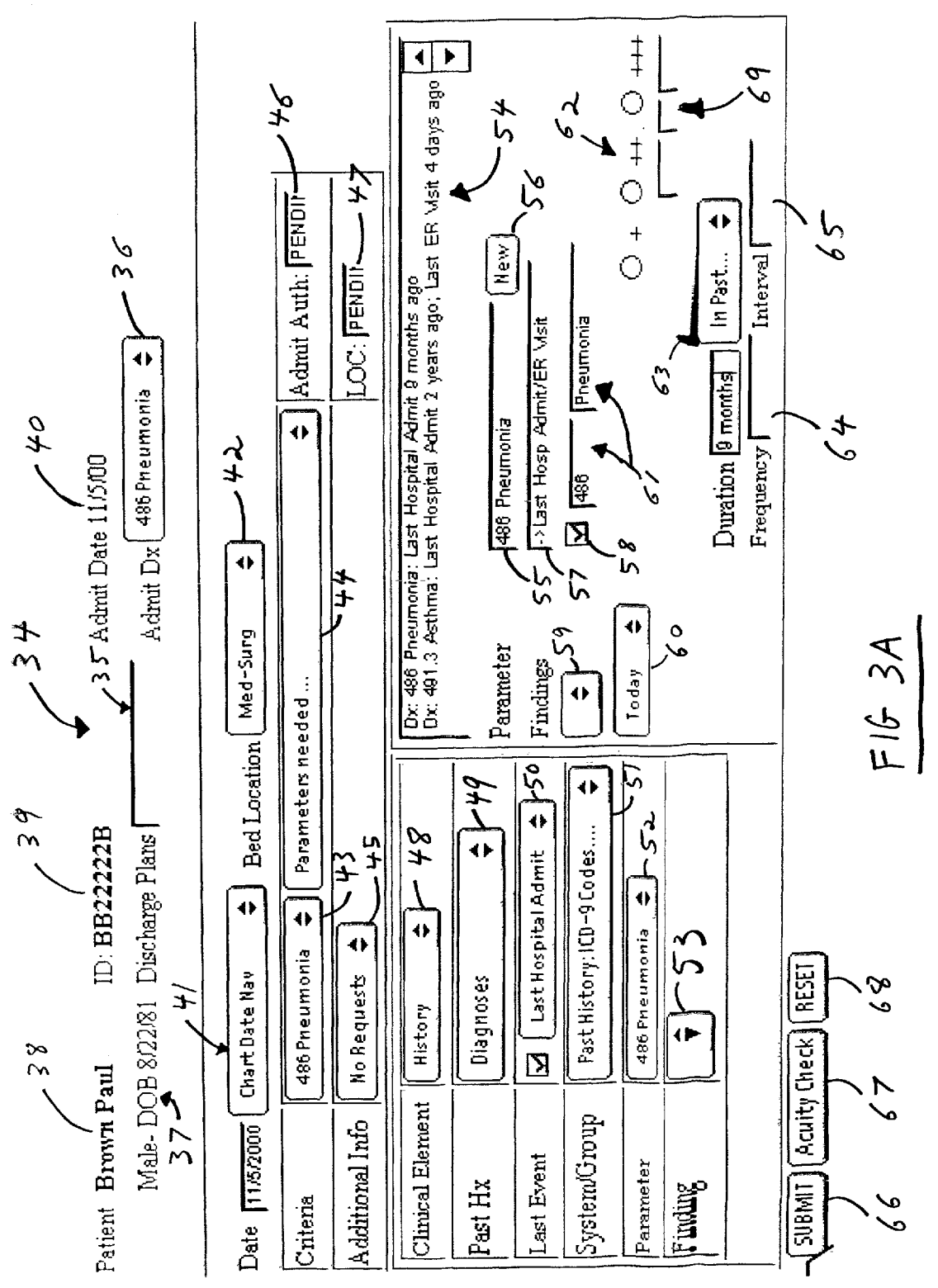

FIG. 3A illustrates the Admission Clinical screen 34 of a utilization system in accordance with the invention. The Admission Clinical screen 34 is used to input the clinical data from the patient's admission exam. This includes historical data including prior surgeries, illnesses, along with the last hospitalizations and emergency room visits for these surgeries and illnesses. For example, historical data includes prior operations, prior diagnosis, prior treatments, history of symptoms, and other physiological data. The Admission Clinical screen includes a header area for displaying patient information. The header area includes a patient name 38, a patient identification number 39, a patient date of birth and gender 37, any discharge plans 35, an admission diagnosis 36, and an admission date 40. The admission diagnosis 36 is preferably set after the patient admission diagnosis is entered in the Admission Face screen of FIG. 2A. Also, the discharge plan 35 is preferably set only after the discharge plan is entered by employing the Discharge Plan screen (discussed below).

A second portion of the Admission Clinical screen is used to select a desired diagnosis for authorization and to select associated criteria. The second portion includes a chart date pop-up list 41, a Patient Location pop-up list 42, a Diagnosis pop-up list 43, a Criteria pop-up list 44, a Level Of Care display box 47, an Authorization display box 46 and an Additional Information Request pop-up list 45. The additional information request pop-up list 45 is preferably used to prompt the user for non-diagnosis related information that is manually reviewed either at the submitting HCP or by the MCO. The Diagnosis pop-up list 43 facilitates the selection of a desired diagnosis. In the context of the Admission Clinical screen 34, the entered diagnosis is an admission diagnosis. The Criteria pop-up list 44 is used to select a criteria that is associated with the desired diagnosis. The Authorization Status display 46 provides the authorization level granted in accordance with the selected criteria. The level of care display box indicates the level of care corresponding to any authorization. In one embodiment, the Criteria pop-up list 44 are preceded by a status designator such as "Needed," "Not Met," and "Met." The status designation changes in accordance with the data entered for the criteria. For example, when a criteria is fist selected, a "Needed" designation is provided. After all data is entered for the criteria, the designation changes to one of "Not Met" or "Met."

A third portion of the Admission Clinical screen 34 is employed to enter diagnosis data in a structured manner. The third portion includes several interlinked pop-up lists. An Element pop-up list 48 is employed to select a clinical element for the encounter. In the Admission Clinical screen 34, the selected element is set to History, corresponding to patient historical information. A System Group pop-up list 51 is provided to select a system group of the selected element. The system group is preferably a subgroup of the element selected from the Element pop-up list. In some context, the system group is the body system corresponding to the medical encounter. A Parameter pop-up list 52 is provided to select a parameter of the selected system group. A Finding pop-up list 53 is used to select one or more findings corresponding to the selected parameter. In the Admission Clinical screen further the parameters do not require a finding. The Admission Clinical screen includes a past history pop-up list 49 to select a medical history event type. The screen also includes A last event pop-up list 50 to select an event. Preferably, the historical data selections are from widely accepted diagnosis and procedure codes. History surgeries and diagnosis, ICD-9 code parameters and CPT-4 code parameters do not require a finding.

In operation, the uses selects either Surgeries or Past Diagnosis from the Past History (Past Hx) pop-up list 49. In one embodiment, the Surgeries are grouped, in the System/Group pop-up lists, by CPT-4 Codes. In another embodiment, the Diagnoses are grouped, in the System/Group pop-up lists, by ICD-9 Codes. Both sets of codes are issued by the AMA. Selecting a CPT-4 code or ICD-9 code in the System/Group pop-up list, enters the code with its attendant surgery or illness.

Each input Surgery or Diagnosis is concatenated with the last hospital admission episode and/or last emergency room visit, by making selections in the Last Event pop list 50, which offers a choice of Last Hospital Admit or Last ER Visit. Interval since the last event is input in the Duration field and Time Unit pop-up list 63. These last events are concatenated onto the Past Surgery or Past Diagnosis and are displayed in the Current Element scroll box 54.

The fourth portion of the Admission Clinical screen 34 includes a display portion and a data entry portion. The display portion is used to display entered parameters for the selected element in the Element pop-up list 48. For this purpose, a Current Element scroll box 54 displays the parameter data along with multiple associated findings. The entry portion includes a Parameter display box 55 for displaying the selected parameter. The Parameter display box 55 is also used as an entry box is for submitting a parameter without using the pop-up list for History and CPT-4 codes and ICD-9 codes or in preparation for submitting a new parameter. A Finding display box 57 is provided for displaying the selected finding data.

Figure 3C:
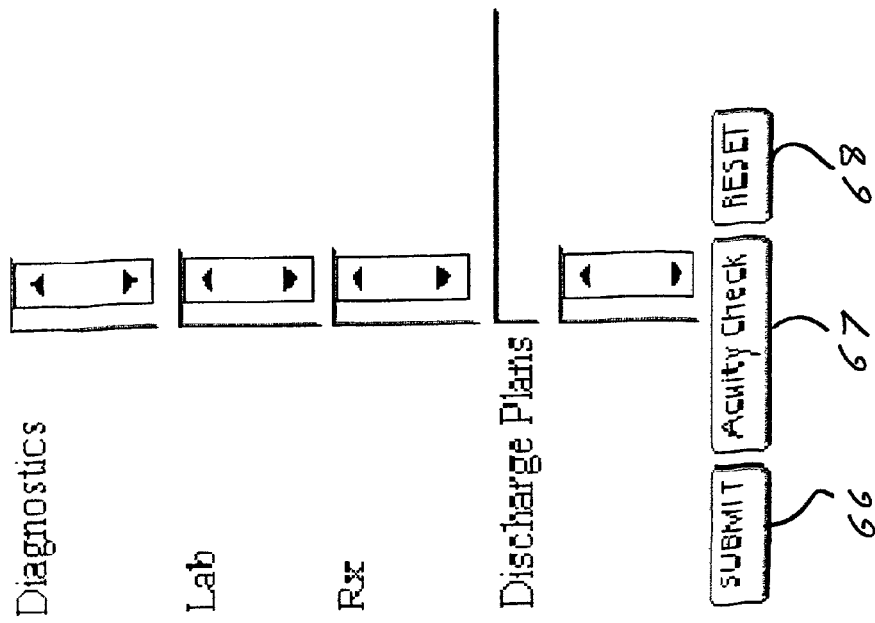
FIG. 3C is a continuation illustration of the chart section of FIG. 3B.

For most findings, selecting a finding in the Finding pop-up list 53 enters the selected Parameter with its finding on a line of the Current Element scroll box (as well as the appropriate Specific Element scroll box in FIG. 3B or 3C). Additional findings for a Parameter are concatenated on the Parameter line after the initial finding.

For findings requiring numerical values (such as lab tests, vital signs), the Parameter and finding are displayed in the Current Element scroll box 54 only after a numeral value has been entered (see below).

Each input findings is also displayed in entry box 61 and entry box 62 and is cumulatively added to the Findings pop-up list 59. Findings not requiring numerical value (such as lab tests, vital signs) are displayed in entry box 62, while entry box 61 displays the finding instance of the Parameter (E.g. Finding_1, Finding_2). For findings requiring numerical values, the finding is displayed in entry box 61 and the clinical value is entered in entry box 62. For example, if entry box 61 displays "hemoglobin," the user would enter "16" in entry box 62 if the patient's lab tests showed a hemoglobin of 16.

Selecting one of the findings in the Findings pop-up list 59 allows modification of, or deletion of, the finding in the Current Element Scroll box. In the Admission Clinical screen 34, the Finding display box 57 is used to display the last event, which was selected from the corresponding Finding pop-up list 50. A pair of entry boxes 61 is used to display the selected parameter and finding, respectively. The entry boxes 61 are also used to marginally enter data for a finding. Entry boxes 61, 62 are also used to enter custom findings not listed in the finding pop-up list 53.

A Time pop-up list 60 is provided to select a time for the event reported. Finally, Duration and Frequency entry boxes 63, 64 are provided for submitting a duration or a frequency for the reported parameter under the Clinical Element Symptoms. An Interval entry box 65 is provided to enter an interval for the reported event. The system preferably responds to the data entry by evaluating the admission diagnosis authorization level. The evaluation is preferably by applying rules to the entered historical data. Accordingly, the user is provided with an indication of appropriateness for the selected admission diagnosis. Such indication is useful for both treatment of the patient and for submitting clinical records to the MCO.

A Chart Date Navigation pop-up list 41 displays all the dates of the patient's current hospitalization and enables the user to navigate to any of these dates to review date for the selected date. Data may be modified for any date except the admission date once the admission has been authorized. The Bed Location pop-up list 42 displays a selection of hospital locations, each which may require a different set of criteria to authorize care for the location. e.g. The standard authorization level for a patient in the hospital is "acute level of care," however the authorization for a patient in an intensive care unit would be "intensive level of care."

An Acuity Check button 67 is provided on the lower portion of the screen to prompt the verifying of data if the clinical event did not receive authorization during data input. Preferably, the system performs rule checks for the criteria associated with the selected diagnosis to determine authorization in a programmatic manner as data is being input. The acuity check preformed is advantageously more comprehensive than the automatic evaluations in response to data entry in fields of the screen. A Submit button 66 is also available for submitting the screen data to the system and navigating back to the Hospital Census screen. Finally, a Reset button 68 is available for resetting the screen selections and entries.

Preferably, the rule associated with the selected criteria is applied to the entered data after the user enters data in all required fields associated with the rule. The authorization status and the status of the criteria are modified in accordance with the result of the rule application. As may be appreciated, because an admission authorization sometimes depends on more than one criteria, a criteria can be met while the authorization status remains as pending status.

Figure 4A:
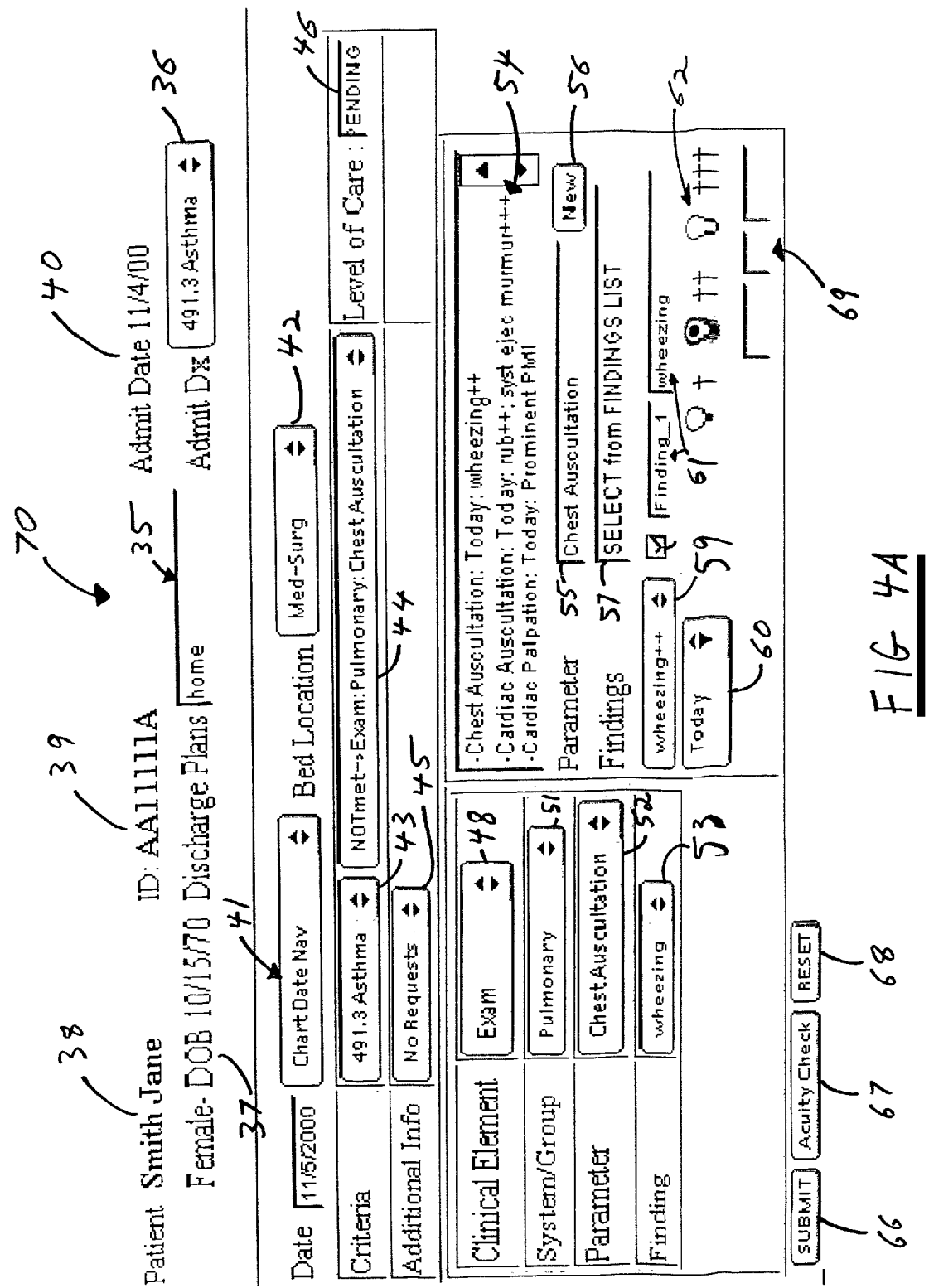
FIG. 4A illustrates a Clinical screen.
Figure 4B:
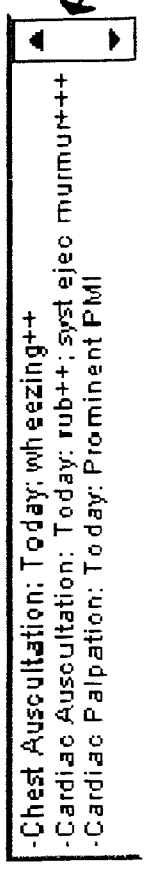
FIG. 4B illustrates a chart section of the Clinical screen of FIG. 4A.
Figure 4B:

FIG. 4A illustrates the Clinical screen 70 of the utilization system. The Clinical screen 70 includes the same header portion as the Admission Clinical screen 34. The Clinical screen 70 also includes the same second portion as the Admission Clinical screen 34. The third portion of the Clinical screen 70 is different from that of the Admission Clinical screen 34. In the Clinical screen, the selection of a criteria from the Criteria pop-up list 44 prompts the navigation of the Element, System Group, and Parameter pop-up lists 48, 51, and 52 to the applicable data for the selected criteria. The user then selects a finding from the Finding pop-up list 53. If data is required for a finding, the user enters the data in the entry portion of the screen. The entry boxes a first box that is used as a placeholder when data requires only a single entry field, and a second box to enter data. The findings available in the findings pop-up list 59 of the data entry portion are the findings that have been previously entered for the parameter. Furthermore, in the data entry portion Finding pop-up list 59, each finding is preferably followed by the associated data for the finding. In the illustrated example, the severity indication from the radio control box is provided following the finding "wheezing." Preferably, when the "Exam" element is selected from the Element pop-up list 48, all possible findings for the particular exam are displayed in the Finding pop-up list 59 of the display portion, whether selected or not, along with any entered values.

The display portion also includes a check box 58 to delete the selected finding from the findings associated with the parameter in the Element scroll box 54. In one embodiment, the data entry portion includes a Severity Selection radio-type control 62. In other embodiments, the data entry portion includes other control boxes as may be required in accordance with the data type assigned to the selected finding. Preferably, selecting an element from the Element pop-up list 48 brings up the element data already entered in the current element scroll box 54. The parameter or finding are advantageously not displayed until minimum data is entered. Accordingly, findings that require a value, in addition to a selection, are not displayed in the current element scroll box 54 until the corresponding value is entered.

FIGS. 3B and 3C and FIGS. 4B and 4C illustrate chart notes portions 80 of the Admission Clinical screen 34 and of the Clinical screen 70, respectively. The illustrated portions 80 are preferably visible to the user when the screen is scrolled down by employing scrollbar controls of a browsing interface. The chart notes portion 80 includes a separate scrollbox display for each element available to the user in the corresponding screen. Each display scrollbox includes the data that was entered for the corresponding element. Preferably, each display scrollbox includes a control whereby when the user selects a data line from the scrollbox, the corresponding data is made available in the entry portion of the corresponding screen and is displayed in the current element scrollbox 54. Accordingly, the user is able to browse the data that was entered for each element and to modify the entered data by selecting the data display line in the chart notes portion 80.

FIG. 5 illustrates a Discharge screen 71. The Discharge screen 71 is used to set patient discharge actions and other post-encounter actions. The disposition screen 71 includes a first portion that displays patient information. The first portion is the same as the first portion of the Clinical screen 70. A second portion of the screen includes a Disposition Location pop-up list 73. The disposition location is the facility or service that the patient requires after discharge. The simplest and most common discharge plan is disposition to home with no post discharge support services. However, many patients require various support services to maintain wellness post discharge at home, or may be discharged to another inpatient facility that provides services at a lower level of care.

A third portion of the screen includes an Item Type pop-up list 74, and a collection of follow up action check boxes 79. The Item Type pop-up list 74 includes a DME entry to select Durable Medical Equipment. The Item pop-up list 75 is used to select an item the item type previously selected. Such Item selections include equipment and treatment plans, depending on the applicable discharge plan. A fourth portion of the screen is used to provide vendor information for the selected item. The fourth portion includes a Vendor Location pop-up list 85, and a Vendor pop-up list 84. A scroll box 72 for entering anticipated clinical status on discharge is also provided. In one embodiment, the selected item and findings for the discharge status conform to a discharge rule. The disposition data in the Disposition pop-up list 72 is preferably provided as part of the header on the Clinical Screen to and on the Admission Clinical screens 34. Preferably, once a vendor is selected, the display area 76 updates with the entered item data. The Discharge screen 71 is also used to enter a discharge plan for a patient.

In operation, the user selects a disposition location for the patient. The location is home, or one of several other post treatment facilities. After selecting a location, the user is presented with corresponding pop-up list entries. For example, when a facility is selected as the location, available post-discharge treatments are provided in the Item pop-up list 74. In one embodiment, the utilization system automatically reviews the discharge plan to ensure that the plan is appropriate to the patient's level of functioning and expected needs at discharge. In another embodiment, the discharge plan is submitted to the MCO for manual review.

FIG. 5B illustrates a chart area of the Discharge screen. As discussed above with reference to FIGS. 3B, 3C, 4B, and 4C, the chart area is a bottom portion of the corresponding screen, which includes individual display scrollboxes for elements of the screen. In the context of the Discharge screen, the chart area 92 includes scrollboxes for Discharge Plans, Clinical Status, Clinical Needs, Exam, and Rx.

FIG. 5C illustrates a Discharge screen 71 with data selections for a post-discharge treatment facility. The selected disposition from the Disposition Location control 73 is Skilled Nursing. The item selected for the disposition is of Needs PRI submission. The vendor location of Nyack is selected. The vendor of Sunrise Nursing Home is selected from the vendor pop-up list. As discussed above, the vendor details are displayed after the vendor is selected from the vendor pop-up list.

Figure 6:
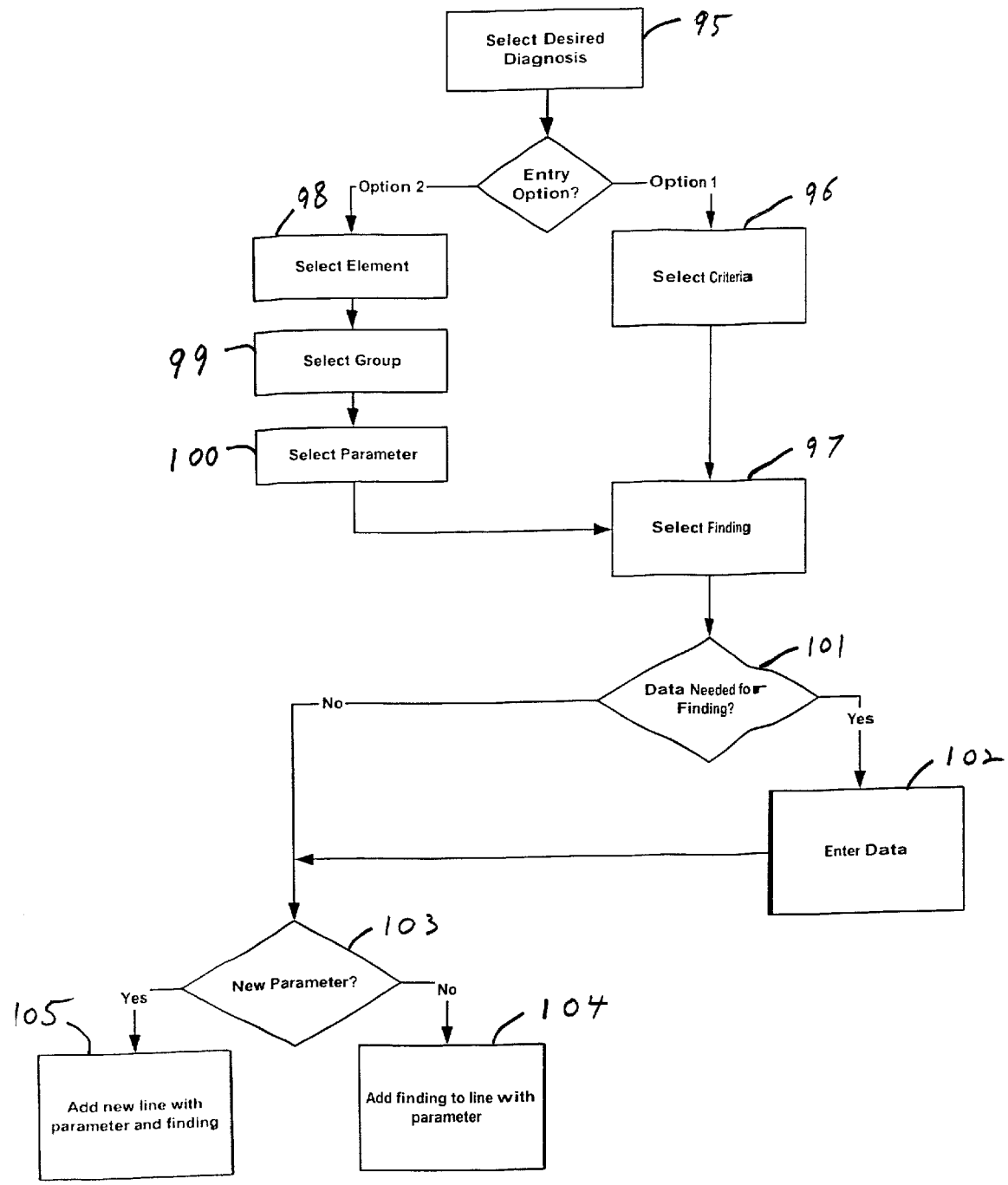
FIG. 6 is a flow diagram illustrating a process for entering diagnosis data in accordance with the invention.

FIG. 6 is a flow diagram illustrating the process for submitting medical encounter data in the Clinical screen 70. The user starts by selecting a diagnosis from the diagnosis pop-up list 43 (step 95). The user has two options in submitting encounter data to the system. A first option is a two-step entry procedure. First, the user selects a criteria from the criteria pop-up list 44 (step 96). The criteria selection results in the automatic population of the element, system group, and parameter pop-up lists 48, 51, and 52. The user then selects from the Finding pop-up list 53 (step 97).

Alternatively, the user employs the second entry option, which is to progress through the hierarchal pop-up lists in the third portion of the Clinical screen 70. The user selects an element from the Elements pop-up list 48 (step 98). The system searches for groups that are associated with the element. Preferably, the navigation module 21 searches the selection database 24 for associated groups. The navigation module 21 then identifies the groups that should be made available in the System Group pop-up list 51. The user then selects a system group from the System Group pop-up list 51. The system then employs the navigation module 21 to identify the parameters associated with the selected system group. The associated parameters are then made available for user selection from the Parameter pop-up list 52. The user selects a parameter from the Parameter pop-up list 52 (step 100). The system then employs the navigation module 21 to identify the data range and format for findings that are available for the parameter. The findings, including the associated data ranges and formats are employed to provide the user with a selection and entry interface for findings. The user then selects a finding from the Findings pop-up list 53 (step 97).

The system then determines if additional data is required for the finding (step 101). If additional data is required for the selected finding, the user employs the provided interface to enter the data (step 102). For example, when the needed data is a severity indication, the user selects a severity from a radio control button.

After receiving all the required data for the selected finding, the system adds the selected finding to the findings associated with the selected parameter. The system determines if the parameter is a new parameter that is not in the parameter list for the current element (step 103). If the parameter is not a new parameter, the finding and any associated data is added to the corresponding line of the parameter list (step 104). If the parameter is a new parameter, the parameter is added as a new line to the parameter list, along with the corresponding finding and any associated data (step 105). In one embodiment, the selected finding, along with its associated data, if any, is added to a display scrollbox where all findings for a parameter are provided on one line of the display box. The system then preferably stores the user entries and proceeds in accordance with user selections to authorize the record or format the record for submission to an authorization agency.

In another embodiment, the data is directly entered by a doctor or a treating nurse. The data is entered by employing a mobile personal data appliance such as a PALM computing device. The mobile device interacts with the server and specially configured user screens to enter patient and treatment data, as discussed above. Therefore, there is no need to use paper data recording that are later entered into the utilization server by an operator.

Preferably, the screens of the utilization system are web page screens. The controls are common web page controls, as is known. The data is preferably provided to the authorization agency as part of digital reporting and records. In one embodiment, a text file is transmitted to the agency on a weekly basis.

In other embodiments, the MCO employs the system only for gathering data from clients without the automatic evaluation of authorization status.

Although the present invention was discussed in terms of certain preferred embodiments, the description is not limited to such embodiments. Rather, the invention includes other embodiments including those apparent to a person of ordinary skill in the art. Thus, the scope of the invention should not be limited by the preceding description but should be ascertained by reference to the claims that follow.

APPENDIX A

Elements Tree

| Element | System/Group | Parameter | Finding |
| --- | --- | --- | --- |
| Symptoms | General | Consitutional | loss of appetite<br>night fevers<br>night sweats<br>weight loss |
| | | Other | cyanosis<br>diaphoresis<br>fever<br>palor<br>tremulousness |
| | HEENT | Vision | blind<br>blind left eye<br>blind right eye<br>blurred<br>diploplia |
| | | Headache | aura<br>episodic<br>persistent<br>steady<br>throbbing |
| | | Pain | sinuses<br>throat |
| | Cardio-Pulmonary | Pain | Char-burning<br>Char-crushing<br>Char-pleuritic<br>Char-pressing<br>Char-sticking<br>Loc-back<br>Loc-left chest<br>Loc-lower jaw<br>Loc-neck<br>Loc-right chest<br>Loc-substernal<br>Onset-at rest<br>Onset-on exertion |

APPENDIX A-continued

Elements Tree

| Element | System/Group | Parameter | Finding |
|---|---|---|---|
| | | | Onset-while sleeping |
| | | | Rad-back |
| | | | Rad-left arm |
| | | | Rad-lower jaw |
| | | | Rad-neck |
| | | | relieved by antacid |
| | | | relieved by nitroglc |
| | | Dyspnea | 1 flight |
| | | | 2 flight |
| | | | at rest |
| | | | minimal exertion |
| | | | None |
| | | | sudden onset |
| | | Orthopnea | 1 pillow |
| | | | 2 pillow |
| | | Sleep | apneic epsiodes |
| | | | daytime somnolence |
| | | | snoring |
| | | Cyanosis | diffuse |
| | | | fingernails |
| | | | lips |
| | | Syncope | unwitnessed |
| | | | witnessed |
| | | Cough | dry |
| | | | unable to raise sput |
| | | | with clear sputum |
| | | | with colored sputum |
| | | | with rusty sputum |
| | | Swelling | abdominal |
| | | | ankle |
| | | | arms |
| | | | diffuse |
| | | | hands |
| | | | legs |
| | Gastro-intestinal | Nausea | continuous |
| | | | post prandial |
| | | Vomiting | bilious |
| | | | daily episodes |
| | | | post prandial |
| | | | projectile |
| | | Pain | Char-colicky |
| | | | Char-intermittent |
| | | | Char-steady |
| | | | Loc-diffuse |
| | | | Loc-LLQ |
| | | | Loc-LUQ |
| | | | Loc-periumbilical |
| | | | Loc-RLQ |
| | | | Loc-RUQ |
| | | | none |
| | | | Onset-2 hrs post pra |
| | | | Onset-half hr post p |
| | | | Onset-nocturnal |
| | | | Rad-back |
| | | | Rad-LLQ |
| | | | Rad-LUQ |
| | | | Rad-RLQ |
| | | | Rad-RUQ |
| | | Diarrhea | blood streaked |
| | | | bloody |
| | | | daily episodes |
| | | | with mucous |
| | | Constipation | last bm (days ago) |
| | | | with narrow bore sto |
| | | Hematemesis | blood streaked |
| | | | bloody |
| | | | coffee grounds |
| | | Rectal Bleeding | melena |
| | | | on toilet paper |
| | | | permeates stool |
| | | | positive occult bloo |
| | | Swelling | abdominal |
| | | | ankle |
| | | | arms |
| | | | diffuse |
| | | | hands |
| | | | legs |
| | | Dysphagia | liquids |
| | | | solids |
| | | Jaundice | non pruritic |
| | | | pruritic |
| | | | with clay stools |
| | Genito-Urinary | Urinary | clots in urine |
| | | | dysuria |
| | | | hematuria |
| | | | nocturia |
| | | | polyuria |
| | | Gyn | LMP (mos) |
| | | | menorrhagia |
| | | | metrorrhagia |
| | | | purulent discharge |
| | Musculo-skeletal | Pain | Loc-ankles |
| | | | Loc-elbows |
| | | | Loc-feet |
| | | | Loc-hands |
| | | | Loc-hips |
| | | | Loc-knees |
| | | | Loc-left |
| | | | Loc-lower back |
| | | | Loc-neck |
| | | | Loc-right |
| | | | Loc-shoulders |
| | | | Loc-upper back |
| | | | Loc-wrists |
| | | | Onset-continuous |
| | | | Onset-on motion |
| | | | Rad-buttocks |
| | | | Rad-legs |
| | | Trauma | abrasion |
| | | | bruised |
| | | | fracture closed |
| | | | fracture open |
| | | | laceration |
| | | | swelling |
| | | Weakness | left foot |
| | | | left hand |
| | | | left side |
| | | | LLE |
| | | | LUE |
| | | | right foot |
| | | | right hand |
| | | | right side |
| | | | RLE |
| | | | RUE |
| | Neuro-Psych | Weakness | left foot |
| | | | left hand |
| | | | left side |
| | | | LLE |
| | | | LUE |
| | | | right foot |
| | | | right hand |
| | | | right side |
| | | | RLE |
| | | | RUE |
| | | Paralysis | left side |
| | | | LLE |
| | | | LUE |
| | | | right side |
| | | | RLE |
| | | | RUE |
| | | Other Impairment | aphasia |
| | | | chokes on swallowing |
| | | | diploplia |
| | | | dysarthria |
| | | | transient visual los |
| | | Mood | anxious |
| | | | danger to others |
| | | | depressed |

APPENDIX A-continued

Elements Tree

| Element | System/Group | Parameter | Finding |
|---|---|---|---|
| Exam | General | Hallucinations | normal |
| | | | suicidal |
| | | | aural |
| | | | visual |
| | | Vital Signs | acute pain |
| | | | diaphoresis |
| | | Observation | labored respirations |
| | | | no acute distress |
| | | | normal respirations |
| | | | pallor |
| | HEENT | Observation | post pharynx obstruc |
| | | | pupils constricted |
| | | | pupils dilated |
| | | | pupils unequal |
| | | Palpation | skull depression |
| | Neck | Observation | rigid |
| | | | supple |
| | | | venous distention |
| | | Auscultation | carotid bruit |
| | | | normal |
| | Heart | Auscultation | diastolic murmur |
| | | | irregular rhythm |
| | | | normal |
| | | | regular rhythm |
| | | | rub |
| | | | systolic murmur |
| | Chest | Observation | flail chest |
| | | | labored |
| | | | normal respiration |
| | | | retractions intercos |
| | | | retractions supraste |
| | | | with accessory muscl |
| | | Palpation | fremitus |
| | | Auscultation | bibasilar |
| | | | diffuse |
| | | | left |
| | | | one third from base |
| | | | rales |
| | | | right |
| | | | ronchi |
| | | | rub |
| | | | wheezing |
| | | Percussion | dullness |
| | | | left |
| | | | right |
| | | | tympany |
| | Abdomen | Palpation | Diffuse |
| | | | guarding |
| | | | LLQ |
| | | | LUQ |
| | | | normal |
| | | | point tenderness RLQ |
| | | | rebound |
| | | | rigidity |
| | | | RLQ |
| | | | RUQ |
| | | | tenderness |
| | | Auscultation | bs absent |
| | | | bs high pitched |
| | | | bs present |
| | | | normal bowel sounds |
| | Rectal | Palpation | bloody stool |
| | | | clay stool |
| | | | mass |
| | | | melena |
| | | | normal |
| | Pelvic | Palpation | adnexal tenderness |
| | | | cervical tenderness |
| | Extremities | Observation | hip external flexion |
| | | | induration |
| | | | inflammation |
| | | | ulcer |
| | | Palpation | ankle edema |
| | | | calf tenderness |
| | | | cold |
| | | | pretibial edema |
| | Neuropsych | Observation | agitated |
| | | | comatose |
| | | | confused |
| | | | depressed |
| | | | obtunded |
| | | | oriented × 3 |
| | | | rousable |
| | Meds IV | Vasopressors | aramine |
| | | | dolbutamine |
| | | | dopamine |
| | | Antibiotics | aminoglycoside |
| | | | amphotericin |
| | | | cephalosporin |
| | | | vancomycin |
| | | | zozin |
| | | Steroids | decadron |
| | | | solucortef |
| | | | solumedrol |
| | | Narcotics | morphine |
| | Orders | Activity | ambulation |
| | | | bed rest |
| | | | oob in chair |
| | | Diet | clear liquids |
| | | | full liquids |
| | | | low carbohydrate |
| | | | low salt |
| | | | npo |
| | | | pureed |
| | | | regular |
| | | Pulmonary Rx | chest physiotherapy |
| | | | mini-nebs |
| | | | nasal O2 |
| | | | venti-mask |
| | | Nursing | ambulate pt |
| | | | I & O |
| | | | turn pt q2h |
| | Indwelling Objects | Nasogastric Tube | gravity |
| | | | low Gumco suction |
| | | Endotracheal Tube | nasal |
| | | | oral |
| | | Chest Tube | air seal |
| | | | wall suction |
| | | Urinary Catheter | |
| | Ventilator | Settings | fiO2 |
| | | | peak pres |
| | | | rate |
| | | | tidal volume |
| | | Mode | assist contol |
| | | | IMV |
| | | Special | CPAP |
| | | | CPAP |
| | Meds Oral | | |
| Lab | Chemistry | Lytes | Sodium |
| | | | Potassium |
| | | | Chlorides |
| | | | HCO3 |
| | | Renal | BUN |
| | | | Creat |
| | | Cardiac | Troponinl |
| | | | CPK |
| | | | CPK-MB |
| | | Liver | Bilirubin |
| | | | Alk Ptase |
| | | | SGOT |
| | | | SGPT |
| | Hema- | WBC | Wbc |

APPENDIX A-continued

Elements Tree

| Element | System/Group | Parameter | Finding |
|---|---|---|---|
| | tology | | Bands |
| | | | Platelets |
| | | Hgb-Hct | Hgb |
| | | | Hct |
| | ABG'S | ABGs | Ph |
| | | | PO2 |
| | | | PCO2 |
| | | | HCO3 |
| | Urine | | Spec Grav |
| | | Urinal-ysis | Wbc |
| | | | Rbc |
| | Micro-biology | | |
| | Stool | | |
| | Toxic-ology | | |
| | Other | | |
| Diagnostics | X-Rays | Skull | fracture |
| | | | normal |
| | | Chest | atelectasis lobar |
| | | | atelectasis segmenta |
| | | | atelectasis subsegme |
| | | | cardiomegaly |
| | | | infiltrate one lobe |
| | | | infiltrates multi lo |
| | | | left lower lobe atel |
| | | | mediatinal shift |
| | | | normal |
| | | | pneumothorax |
| | | | pulmonary edema |
| | | | vascular congestion |
| | | Abdomen | air fluid levels |
| | | | dilated small bowel |
| | | | normal |
| | | | pneumoperitoneum |
| | | Hip | fracture femoral nec |
| | | | normal |
| | | Tibia | fracture closed |
| | | Fibula | fracture open |
| | | | normal |
| | CAT Scans | Head | acute cva |
| | | | mass |
| | | | midline shift |
| | | | normal |
| | | | subarachnoid bleed |
| | | | subdural bleed |
| | | Chest | atelectasis lobar |
| | | | atelectasis segmenta |
| | | | enlarged hilum |
| | | | infiltrate multi lob |
| | | | infiltrate one lobe |
| | | | mass |
| | | | mediastinal shift |
| | | | normal |
| | | | pulmopnary edema |
| | | | vascular congestion |
| | | Abdomen | abcess |
| | | | appendicitis |
| | | | ascites |
| | | | dilated small bowel |
| | | | diverticulitis |
| | | | normal |
| | | | pneumoperitoneum |
| | MRI'S | Head | acute cva |
| | | | mass |
| | | | midline shift |
| | | | normal |
| | | | subarachnoid bleed |
| | | | subdural bleed |
| | Ultra-sound | Gall-bladder | dilated com bile duc |
| | | | normal |
| | | | sludge |
| | | | stones |
| | | Cardiac | ejection fraction |
| | | | pericardial effusion |
| | | | thrombus |
| | | | valve vegetation |
| | Radio-nucleide | Lung Vent Perf Scan | high prob embolism |
| | | | low prob embolism |
| | | | medium prob embolism |
| | | | normal |
| | Endoscopy | | |
| | Pulmonary Function | | |
| | Cardiac Studies | | |
| | Pathology | | |

What is claimed is:

1. A method for collecting patient clinical encounter information comprising the steps of:
   storing, on a computer-readable medium operatively connected to a server, computer-executable instructions comprising:
   a) a navigation module;
   b) a verification module; and,
   c) a user interface comprising a plurality of fields, at least one of the fields comprising a pop-up list, the arrangement of the plurality of fields being fixed and arranged as on a clinical chart;
   transmitting, via a network, the navigation module, the verification module and the user interface from the server to a client device;
   causing the client device to display the user interface, including the plurality of fields, within a single screen to a user, the user interface facilitating the entry of patient clinical encounter information into the plurality of fields by not requiring the user to scroll the user interface within the single screen;
   receiving, via the user interface displayed on the client device, patient clinical encounter information from the user;
   causing the navigation module on the client device to modify the contents of at least one of the plurality of fields in response to the received patient clinical encounter information;
   receiving, via the user interface displayed on the client device, at least one diagnosis selected by the user via the user interface;
   causing the verification module on the client device, to determine an authorization level for the at least one diagnosis by referring to the contents of at least a subset of the plurality of fields; and,
   receiving on the server, via the network, the patient clinical encounter information and the at least one diagnosis from the client device after the determination of the authorization level for the at least one diagnosis by the verification module.

2. The method of claim 1, the computer-executable instructions stored on the computer-readable medium and transmitted to the client device further comprising instructions for one or more criteria corresponding to a diagnosis, the criteria being displayed to the user in at least one of the plurality of fields.

3. The method of claim 2, the computer-executable instructions stored on the computer-readable medium and transmitted to the client device further comprising instructions for determining of an authorization level by referring to the criteria.

4. The method of claim 1, the computer-executable instructions stored on the computer-readable medium and transmitted to the client device further comprising instructions for a rule database, the rule database being employed by the verification module when determining the authorization level on the client device.

5. The method of claim 4, the rule database storing at least two levels of rules, the levels comprising:
   a criteria level, the criteria level rules determining a criteria status by referring to data from at least one of the plurality of fields; and,
   a diagnosis level, the diagnosis level rules determining a diagnosis authorization level by referring to the criteria status of at least one criteria level rule.

6. The method of claim 1, at least a subset of the plurality of fields being related in a hierarchical manner, the navigation module changing the content of at least one of the plurality of fields based on selections made therein by the user.

7. The method of claim 6, the verification module further comprising a plurality of criteria rules, the verification module evaluating the criteria rules to determine whether the patient clinical encounter information meets one or more criteria for determining an authorization level.

8. The method of claim 1, the instructions being transmitted via the Internet.

9. Computer readable media having instructions for determining the appropriateness of patient clinical encounter information tangibly stored thereon, the instructions, when executed by a computer, comprising instructions for:
   causing a client device to display a criteria selection interface to a user, the criteria selection interface allowing the user to select a diagnosis-based criteria, the criteria selection interface being presented in a clinical format that is familiar to clinicians and healthcare reviewers, the criteria selection interface being presented to the user within a single screen such that the user does not have to scroll within the single screen while selecting criteria, the client device retrieving the criteria selection interface from a server via the Internet;
   receiving diagnosis related data from the user;
   causing the client device to apply a verification rule to the received diagnosis related data, the verification rule providing a verification result, the verification result providing an authorization level for each selected criterion in the criteria selection interface.

* * * * *